United States Patent [19]

Killian et al.

[11] Patent Number: 5,569,581
[45] Date of Patent: Oct. 29, 1996

[54] ALTERATION AND PREDICTION OF MALE FERTILITY USING SEMINAL PLASMA AND ITS COMPONENTS

[75] Inventors: Gary Killian; David Chapman; Aida Cancel, all of State College, Pa.; Margaret A. Henault, Miami, Fla.

[73] Assignee: The Penn State Research Foundation, University Park, Pa.

[21] Appl. No.: 154,226

[22] Filed: Nov. 17, 1993

[51] Int. Cl.$^6$ ..................................................... C12Q 1/00
[52] U.S. Cl. ................................ 435/4; 435/806; 424/520
[58] Field of Search .................................. 435/2, 4, 806; 424/520, 531; 514/8, 21

[56] References Cited

PUBLICATIONS

Baas J., Factors in Seminal Plasma of Bulls That . . . J Reprod Fert (1983) 68 275–280.
Averlof E., Serum Factors Stimulate The . . . Int J of Andrology 1989 vol. 12 pp. 124–130.
Al–Aghbari, A., Demonstration of a Link Between . . . Dis Ab Int vol. 53 #6 Dec. 1992 pp. 2595–B–6.
Tie J., An Analysis of Low Side MW Proteins In . . . Japenese J of Legal Medicine 47(4) Aug. 1993 pp. 295–301.

*Primary Examiner*—William H. Beisner
*Assistant Examiner*—Ralph Gitomer
*Attorney, Agent, or Firm*—Thomas J. Monahan

[57] ABSTRACT

Two-dimensional polyacrylamide gel electrophoresis of seminal plasma samples indicate that two proteins (26 kDa, pI 6.2; 55 kDa, pI 4.5) predominated in higher fertility bulls and two proteins (16 kDa, pI 4.1; 16 kDa, pI 6.7) predominated in lower fertility bulls. A regression model was developed to predict bull fertility using the four fertility-associated protein densities. A plot of actual bull fertility versus that calculated by this model was linear and positively correlated (r=0.89). These findings indicate that bull seminal plasma contains fertility-associated proteins which are predictive of bull fertility. Additionally, the ability of seminal plasma to alter the in vitro fertility of ejaculated bull sperm was examined using a sperm penetration assay for zona-free bovine oocytes. Washed, ejaculated sperm from bulls of below (low) or above average (high) fertility were mixed with seminal plasma from the same bull, or with seminal plasma from a bull of contrasting fertility. Washed sperm exposed to seminal plasma from high fertility bulls penetrated more oocytes than when those sperm were mixed with seminal plasma from low fertility bulls (p<0.01). Mixing low fertility sperm with high fertility seminal plasma generally improved penetrating ability compared to low fertility sperm mixed with low fertility seminal plasma.

2 Claims, 5 Drawing Sheets

ALTERATION AND PREDICTION OF MALE FERTILITY USING SEMINAL PLASMA AND ITS COMPONENTS

GOVERNMENT SPONSORSHIP

This invention was made with Government support under Grant 90-37240-5512 awarded by the U.S. Department of Agriculture. The Government has certain rights in the invention.

BACKGROUND OF THE INVENTION

The present invention relates to the field of animal husbandry. More specifically it relates to novel methods of predicting and altering male fertility. It presents four novel seminal plasma proteins involved in the fertility of bulls. These proteins may have a variety of applications including use in fertility prediction and fertility alteration. The present invention describing the alteration of male fertility by contacting semen with seminal plasma of different characteristic may prove especially useful in man, either to improve male fertility with artificial insemination, or to decrease male fertility when used as or with contraceptive agents or devices.

Males with suboptimal fertility are a concern in humans as well as agricultural animals. Although males typically labeled as subfertile or infertile are characterized by poor sperm motility, high numbers of abnormal sperm or inadequate freezability, the subfertile male with normal semen parameters remains an enigma. For these males, the factors contributing to their subfertility are largely unknown.

Collectively, the various studies comparing the effects of seminal plasma on the fertility of caudal or ejaculated sperm are inconclusive. Mouse and rabbit sperm have been reported to become more fertile after addition of a low molecular weight factor from human seminal plasma [Gaur R. D., Talwar G. P., 1975, Further studies on the fertility promoting factor from human seminal plasma. Int. J. Fertil.; Vol. 20, pp 133–136]. Seminal plasma components, especially those from the seminal vesicles, have been found to augment fertility in the rat [Curry, P. T. and R. W. Atherton, 1990, Seminal vesicles: development, secretory products, and fertility. Arch. Androl. Vol. 25, pp 107–113]. Changes in seminal plasma composition resulting from removal of some or all of the accessory sex glands, also may be detrimental to fertility in the rat [Queen, K., C. B. Dhabuwala and C. G. Pierrepoint, 1981, The effect of the removal of the various accessory sex glands on the fertility of male rats. J. Reprod. Fert. Vol. 62, pp 423–426], hamster [Chow, P. H., S. F. Pang, K. W. Ng and T. M. Wong, 1986, Fertility, fecundity, sex ratio and the accessory sex glands in male golden hamsters. Int. J. of Androl. Vol. 9, pp 312–320]and mouse [Pang, S. F., P. H. Chow and T. M. Wong, 1979, The role of the seminal vesicle, coagulating glands and prostate glands on the fertility and fecundity of mice. J. Reprod. Fertil. Vol. 56, pp 129].

In contrast, several studies have concluded that sperm exposure to seminal plasma depresses sperm motility in the boar [Iwamoto, T., A. Tsang, M. Luterman, J. Dickson, E. deLamirande, M. Okuno, H. Mohri and C. Gagnon, 1992, Purification and characterization of a sperm motility-dynein ATPase inhibitor from boar seminal plasma. Molec. Reprod. and Devel. Vol. 31, pp 55–62], human [Iwamoto, T. and C. Gagnon, 1988, Purification and characterization of a sperm motility inhibitor in human seminal plasma. J. Androl. Vol. 9, pp 377–383], bull, ram, goat [Dott, H. M., R. A. P. Harrison and G. C. A. Foster, 1979, The maintenance of motility and the surface properties of epididymal spermatozoa from bull, rabbit and ram in homologous seminal and epididymal plasma. J. Reprod. Fert. Vol. 55, pp 113–124], stallion, and rabbit [Corteel J. M., 1980, Essets du Plasma Seminal sur la Survie et la Fertilite des Spermatozoides Conserves In Vitro. Reprod. Nutr. Develop. Vol. 20, pp 1111–1123]. Decreases in sperm fertility after exposure to seminal plasma components also have been reported for humans [Andhya et al., 1987, Purification and partial chemical characterization of a glycoprotein with antifertility activity from human seminal plasma. Biol. Reprod. Vol. 36, pp 511–521] and rabbits [Chang, M. C., 1957, A detrimental effect of seminal plasma on the fertilizing capacity of sperm. Nature. Vol. 179, pp 258–259].

Studies evaluating the seminal plasma characteristics of individuals and their relationship to fertility are limited. When compared to fertile men, infertile men have been reported to be missing seminal plasma proteins resolved by two dimensional gel electrophoresis [Sadowski, T. and B. J. Rogers, 1985, Two-dimensional electrophoetic patterns of seminal plasma proteins from fertile and infertile men. Biol. Reprod. Suppl. 1. Vol. 32, Abstr.#130]. Distribution of some heparin binding protein have been found to differ between seminal plasma of high and low fertility bulls [Kandell, R. L., M. E. Bellin, H. E. Hawkins and R. L. Ax, 1992, Bull fertility related to distributions of heparin binding proteins in sperm membranes and seminal plasma. J. Androl. Suppl. Abst. #51]. The presence, absence or the critical concentration of proteins in seminal plasma could potentially be responsible for the effects of seminal plasma on sperm fertility.

One difficulty with previous studies attempting to establish an effect of seminal plasma on animal fertility has been the lack of good fertility data on the individuals in question. In addition, relatively small effects of seminal plasma on fertility may escape detection because of assay insensitivity. The studies described in this patent application overcome these potential problems by using cull dairy bull sires with reliable fertility data, and by using a heterospermic zona-free bovine oocyte penetration assay which negates the effect of egg variation and facilitates the detection of small differences in fertility. The goal of these studies was to determine if the in vitro fertility of ejaculated sperm could be altered by exposure to seminal plasma from a bull of contrasting fertility. In addition the possibilities of predicting male fertility based on studies of seminal plasma proteins were examined and resulted in developing a method allowing for such prediction.

Dairying is the major agricultural enterprise. A major factor affecting the success of dairying has been the increased milk production per cow which has resulted from the artificial insemination (AI) of cows with semen from genetically superior sires. The average doubling of milk production per cow over the last 40 years is largely attributable to the genetic selection and breeding services provided by the AI industry.

Reproduction is a vital factor in determining the profitability of a dairy herd. Successful reproduction not only produces a calf which may be used to replace older less productive cows in the herd, but it also ensures that the cow will continue to produce milk. A cow will only begin to lactate effectively after calving.

The ideal time interval between calves for cows can vary depending on climate and other factors. If this interval is prolonged because cows fail to conceive during the estrous cycle (about 21 days for each failed conception), it costs farmers in feed, lost milk production and decreased milk yields.

A significant factor contributing to the reproductive efficiency of a dairy cow herd is the fertility of the semen used to inseminate the cow. The AI industry is able to reliably assess the fertility of the semen of individual bulls, because relatively few bulls are used to breed large numbers of cows. The fertility value involves an estimate of the percentage of cows becoming pregnant after being bred with semen from a particular bull. Sires currently in use for AI in this country range in fertility from 55 to 80%. The use of semen from bulls of lower fertility results in a longer than average calving interval for the cow herd, which is more costly to the farmer. It is estimated that using lower fertility bulls results in a minimal loss of 500 lbs of milk production per year per cow, as well as the cost of feeding for non-productive animals.

The reasons the AI industry does not eliminate the lower fertility bulls is due to economics. Currently the AI industry has no method for determining if a bull is subfertile until after the investment of $100,000 or more has been made for the purchase, raising, and maintenance of the bull for 3-4 years until his genetic worth is known. The industry is quite competitive, and semen marketing focuses on the genetic characteristics of milk production of the daughters sired by the bull. If a bull produces daughters with highly desirable genetic characteristics for producing milk, semen from that bull will be in demand. These "high demand" bulls are what those in the AI industry hope to discover, because they can make the difference between a profit or loss for the entire company.

Therefore, once a genetically superior sire has been identified it will only be eliminated from the bulls providing semen for AI if its fertility is extremely poor. Bulls that are 5-15% below average fertility or "subfertile" will still be retained if the characteristics of their daughters are in demand.

The applicants invention presents some new ways of solving the problems outlined above. It provides a novel method for predicting fertility based on the testing of the protein make-up of seminal plasma. It also provides a method for improving fertility of sperm obtained from low fertility bulls. The latter procedure involves harvesting seminal plasma from very high fertility bulls, and using it, or components of it, to treat sperm from bulls with average or below average fertility. The native seminal plasma is removed from the sperm, which is then resuspended in seminal plasma or other medium supplemented with components thereof, obtained from high fertility bulls. The four major seminal plasma proteins involved in the fertility of semen have been identified. The instant invention allows for improvement of fertility of lower fertile but high demand bulls with the seminal plasma or component through obtained from high fertility bulls, which are not necessarily high demand animals.

By the way of background, semen consists of both sperm and seminal plasma. Male fertility is influenced by inherited factors directly associated with the sperm. Reports for several species suggest that seminal plasma contains factors which also influence male fertility. These studies were generally based on comparisons of seminal plasma composition between males of differing fertility [Constentino M. J., Emilson L. B. V., Cockett A. T. K., 1984, Prostaglandins in semen and their relationship to male fertility: A study of 145 men. Fertil Steril; Vol. 41, pp 88–94, Sandowski T., Rogers B. J., 1985, Two-dimensional electrophoretic patterns of seminal plasma proteins from fertile and infertile men. Biol Reprod, Vol. 32, (suppl 1), p 102, Jeyendran R. S., Van der vern H. H., Rosecrans R., Perez-Pelaez M., Al-Hasani S., Zaneveld L. J. D., 1989, Chemical constituents of human seminal plasma: Relationship to fertility. Andrologia, Vol. 21, pp 423–428, Panidis D., Rousso D., Pappas C., Kalogeropoulos A., 1991, Seminal plasma transferfin: does it help in the diagnosis of fertility. J. Obst. Gyn., Vol. 11, pp 211–214, Autiero M., Sansone G., Abreccia P., 1991, Relative ratios of lactoferrin. albumin, and acid phosphatase seminal levels as sperm quality markers in fertile and infertile men. J. Androl., Vol. 12, pp 191–200, Kandell R. L., Bellin M. E., Hajokins H. E., Ax R. L., 1992, Bull fertility was related to distribution of heparin binding proteins in sperm membrane and seminal plasma. J. Androl., Vol. 13(suppl 1), p 30, ] or the isolation of factors from seminal plasma which facilitate or inhibit sperm capacitation, fertilization, and related events [Dukelow W. R., Cheinoff H. N., Williams W. L., 1967, Properties of decapacitation factor and presence on various species. J. Reprod. Fert., Vol. 14, pp 393–399; Hunter A. G., Nornes H. O., 1969, Characterization and isolation of a sperm coating antigen from rabbit seminal plasma with capacity to block fertilization. J. Reprod. Fertil. Vol. 20, pp 419–427, Eng L. E., Oliphant G., 1978, Rabbit sperm reversible decapacitation by membrane stabilization with a highly purified glycoprotein from seminal plasma. Biol. Reprod., Vol. 19, pp 1083–1094, Reddy J. M., Stark R. A., Zaneveld L. J. D., 1979, A high molecular weight antifertility factor from human seminal plasma. J. Reprod. Fert.; Vol. 57, pp 437–446, Gaur R. D., Talwar G. P., 1975, Further studies on the fertility promoting factor from human seminal plasma. Int. J. Fertil., Vol. 20, pp133–136, Shivaji S., Bhargava P. M., 1987, Antifertility factors of mammalian seminal fluid. BioAssays, Vol. 7 pp 13–17, Audhya T., Reddy J., Zaneveld L. J. D., 1987, Purification and partial chemical characterization of a glycoprotein with antifertility activity from human seminal plasma. Biol. Reprod. Vol. 36, pp 511–521, Miller D. J., Winer M. A., Ax R. L., 1990, Heparin-binding proteins from seminal plasma bind to bovine spermatozoa and modulate capacitation by heparin. Biol. Reprod., Vol. 42, pp 899–915].

Antifertility factors from seminal plasma have been described for several species and include decapacitation factors purified to various degrees [Shivaji S., Scheit K. H., Bhargava P. J., 1990, Proteins of Seminal Plasma. New York: John Wiley and Sons, Inc.; pp 332–33, ] human antifertility factor 1 (AFl) [Reddy J. M., Stark R. A., Zaneveld L. J. D., 1979, A high molecular weight antifertility factor from human seminal plasma. J. Reprod. Fert., Vol. 57, pp 437–446, Audhya T., Reddy J., Zaneveld L. J. D., 1987, Purification and partial chemical characterization of a glycoprotein with antifertility activity from human seminal plasma. Biol. Reprod.; Vol. 36, pp 511–521, Reddy J., Audhya T., Goodpasture J. C., Zaneveld L. J. D., 1982, Properties of a highly purified antifertility factor from human seminal plasma. Bio. Reprod., Vol. 27, pp 1076–1083, ], rabbit acrosome stabilizing factor (ASF) [Eng L. E., Oliphant G., 1978, Rabbit sperm reversible decapacitation by membrane stabilization with a highly purified glycoprotein from seminal plasma. Biol. Reprod., Vol. 19, pp 1083–1094, ] and bull seminal plasmin (SPLN) [Shivaji S., Bhargava P. M., 1987, Antifertility factors of mammalian seminal fluid. BioAssays, Vol. 7, pp 13–17, ]. Generally, these factors are believed to inhibit sperm capacitation, the acrosome reaction or acrosomal enzymes and are believed to ultimately interfere with fertilization.

Recent studies [Miller D. J., Winer M. A., Ax R. L., 1990, Heparin-binding proteins from seminal plasma bind to bovine spermatozoa and modulate capacitation by heparin. Biol. Reprod., Vol. 42, pp 899–915, Nass S. J., Miller D. J., Winer M. A., Ax R. L., 1990, Male accessory sex glands produce heparin-binding proteins which bind to cauda epididymal spermatozoa and are testosterone-dependent. Mol. Reprod. Dev., Vol. 25, pp 237–246] have suggested that heparin-binding proteins in bull seminal plasma are taken up by cauda epididymal sperm membranes. Because other studies have indicated that the ability of sperm to bind heparin and other glycosaminoglycans is correlated with semen quality and fertility [Ax R. L., Lenz R. W., 1987, Glycosaminoglycans as probes to monitor differences in fertility of bulls. J. Dairy Sci., Vol. 70, pp 1477–1486, Vasquez J. M., Winer M. A., Ax R. L., Boone W. R., 1989, Correlation of human spermatozoa heparin binding with the zona-free hamster egg in vitro penetration assay. Am. J. Obstet. Gynecol., Vol. 160, pp 20–26, Blottner S., Nehring H., Torner H., 1990, Individual differences in capacitation of bull spermatozoa by heparin in vitro. Relationship to Fertility. Theriogenology, Vol. 34, pp 619–628], heparin- binding proteins in seminal plasma may positively influence fertility.

The applicants developed an interest in this topic after surveying the fertility of reproductively "normal" dairy bulls primarily housed at artificial breeding cooperatives in Pennsylvania and New York. In vivo fertility data summarized for 131 bulls with normal semen parameters, as assessed by laboratory evaluation, indicated that the fertility of the bull population followed a distribution ranging from 8.5 below to 5.4 percentage points above an average fertility designated as zero (FIG. 1). This relatively small range of fertility differences among bulls in the normal population was distinguishable because fertility data were available for individual bulls based on more than 1,000 breedings by artificial insemination. The applicants are not aware of any other species for which such data are available on individual sires. These circumstances provide a unique animal model for the study of factors contributing to the relative fertility of the normal male.

Current genetic selection criteria of dairy as well as beef bull sires is based largely on milk and beef production of the offsprings. Genetic selection does not focus on bull fertility due to the lack of a method to predict bull fertility prior to the obtaining of the second generation data. This practice results in a wide range of fertilities of dairy and beef sires and significant losses to the farmers and breeders due to inefficient reproduction. The presented invention will significantly raise fertility of semen being sold for artificial insemination, without affecting current genetic selection practices.

SUMMARY OF THE INVENTION

In accordance with present invention, four seminal plasma proteins and methods related thereto are presented. The proteins which can be characterized as male fertility factors have been identified in two dimensional gel chromatography and have been proven to correlate with the fertility of the bulls. These novel proteins can find use in a variety of applications including prediction of bull fertility, and methods for improving male fertility by changing the level of proteins in seminal plasma.

Another aspect of this invention is a novel approach to alter fertility of the male plasma by exposing it to seminal plasma from donors of contrasting fertility.

OBJECTS OF THE INVENTION

An object of this invention is to provide novel proteins which can influence male fertility.

Another object of this invention is to provide a method for predicting male fertility by testing the levels of proteins in the seminal plasma.

Yet another object of this invention is to provide a method of altering the fertility of male sperm by exposing semen to seminal plasma or fertility proteins of donors of contrasting fertility.

It is also an object of this invention to develop methods of using the proteins. These and advantages of this invention over prior art and a better understanding of its use will become readily apparent from the following description.

DETAILED DESCRIPTION OF THE INVENTION

Figure 1:
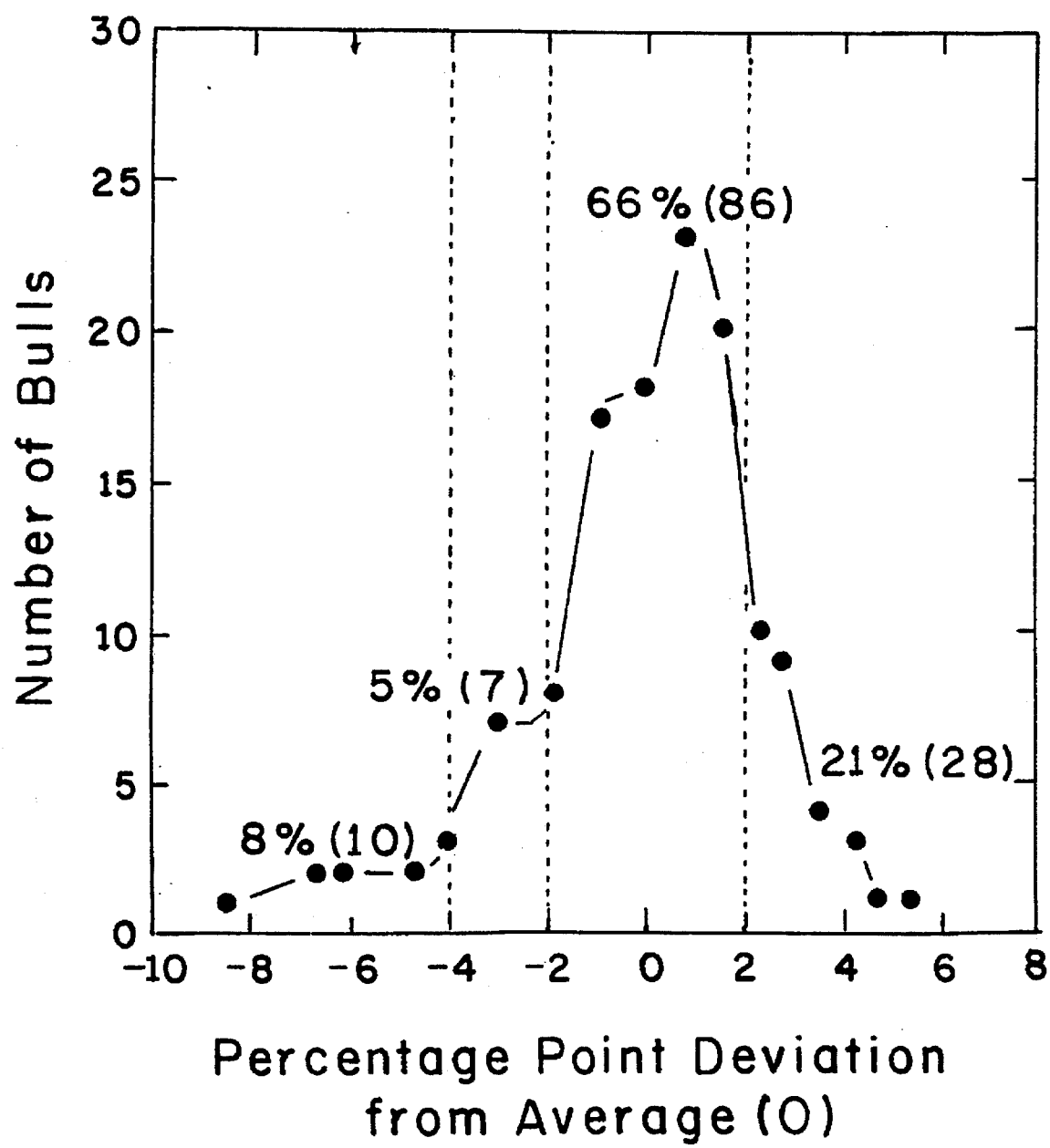
FIG. 1. Plot of number of bulls versus fertility for a population of 131 production dairy bulls, housed at artificial insemination cooperatives in the northeast. Bull fertilities are expressed as a percentage point deviation from the average fertility of the bulls at the AI center where the bulls were housed. Average fertility for purposes of this study was designated as equal to 0.0. The percentage and number () of bulls grouped by fertility level are separated by a vertical dotted line on the plot.

The present invention describes the evidence of correlation between fertility and four seminal plasma proteins in bulls. During the course of detailed studies involving the investigation of bull fertility, the involvement of four seminal plasma proteins in the male fertility was demonstrated. The support for this new finding and ways of using it commercially are described herein.

A detailed embodiment of the present invention involving bull seminal plasma proteins 26 kDa, pI 6.2; 55 kDa, pI 4.5 and 16 kDa, pI 4.1; 16 kDa, pI 6.7 is herein disclosed. However it is understood that the preferred embodiment is merely illustrative of the invention which may be embodied in various forms and applications accordingly, specific structural and functional details disclosed herein are not to be interpreted as limiting, but merely as a support for the invention as claimed and as appropriate representation for the teaching one skilled in the art to variously employ the present invention in any appropriate embodiment.

This study was undertaken to determine whether bovine seminal plasma contained protein markers associated with bull fertility, and whether these markers were of value in predicting bull fertility. Seminal plasma was obtained from 35 Holstein bulls of known fertility. Two-dimensional polyacrylamide gel electrophoresis of seminal plasma samples indicate that two proteins (26 kDa, pI 6.2; 55 kDa, pI 4.5) predominated in higher fertility bulls and two proteins (16 kDa, pI 4.1; 16 kDa, pI 6.7) predominated in lower fertility bulls. Densitometry data for these proteins in individual samples were combined for bulls grouped by fertility level. Average density of the 26 kDa protein was significantly greater in seminal plasma of high fertility bulls, and high fertility seminal plasma also contained more of the 55 kDa protein than average and below average fertility bulls. Below average and low fertility bull seminal plasma had significantly more of both 16 kDa proteins than average and high fertility bulls. A regression model was developed to predict bull fertility using the four fertility-associated protein densities. A plot of actual bull fertility versus that calculated by this model was linear and positively correlated ($r=0.89$). These findings indicate that bull seminal plasma contains fertility-associated proteins which are predictive of bull fertility.

To determine if the fertility of ejaculated sperm could be affected by exposure to seminal plasma from a bull of contrasting fertility, sperm from a bull were washed and either incubated with his own (homologous) seminal plasma or seminal plasma from another bull (heterologous) of contrasting fertility. These differently treated sperm were stained and competed to penetrate the same zona-free bovine oocytes after heterospermic insemination in vitro.

The objective of a second series of experiments was to determine if the relative fertilities of high and low fertility sperm remain the same after mixing both with low fertility seminal plasma. Sperm from high and low fertility bulls were mixed with low fertility seminal plasma, homologous or heterologous to the low fertility bull in each comparison and relative fertility was measured using the zona-free bovine oocyte penetration assay.

To determine the effect of seminal plasma from a lower fertility bull on the in vitro fertility of sperm from a higher fertility bull, washed sperm from 6 different bulls with fertilities of 0.4 to 8.0 points above the average were incubated with either homologous seminal plasma, or seminal plasma from a bull of lower fertility. Overall, high fertility sperm incubated in homologous seminal plasma penetrated significantly more oocytes than high fertility sperm incubated in seminal plasma from lower fertility bulls ($p<0.01$;). Nine of eleven comparisons showed that sperm incubated in high fertility seminal plasma had an oocyte penetrating advantage. The one comparison indicated that high fertility sperm exposed to low fertility seminal plasma penetrated more oocytes than the same sperm incubated in high fertility seminal plasma. One comparison showed no advantage of either type of sperm.

Incubation of low fertility sperm with either low homologous or high fertility seminal plasma resulted in an overall improvement in fertility of subfertile sperm by seminal plasma from higher fertility bulls. Trials were conducted using sperm from bulls ranging in fertility from −3.3 to −23.4 points below the AI center average. An improvement in fertility was achieved in 5 out of 10 cases. The remaining 5 cases showed an oocyte penetrating advantage of sperm exposed to low fertility homologous seminal plasma.

Interestingly, when this experiment was changed so that high or average fertility sperm were incubated with low fertility seminal plasma and competed with low fertility sperm incubated in homologous seminal plasma, the low fertility sperm generally had a significant advantage over the high ($p=0.0012$;). In 3 of 4 cases, the low fertility sperm prevailed over the high fertility sperm.

To eliminate the bias imposed by using homologous seminal plasma, a low fertility seminal plasma pool foreign to bulls being tested was used. In three out of four comparisons, the high fertility sperm penetrated more oocytes.

EXAMPLE 1

Obtaining and Preparation of Seminal Plasma

Samples of seminal plasma were obtained for protein analyses from 35 mature Holstein bulls of known reproductive history. These bulls were a subset of those represented in FIG. 1.

Fertility data on each bull were provided by the AI center and based on breeding records for more than 1,000 inseminations using frozen semen. Because the method of preparing fertility data varied slightly among the AI centers, data for each bull were expressed as a percentage point deviation from the average fertility for all production bulls at that AI center sampled during the same period. To maximize the possibility of detecting differences among bulls associated with fertility, the subset of bulls, on which seminal plasma analyses were conducted were selected to include adequate numbers of bulls in each fertility level as shown separated by vertical lines in FIG. 1. Also, this selection process was influenced by the availability of samples from the cooperating AI centers. For the 35 bulls supplying seminal plasma for analysis, the percentage point deviations ranged from −6.6 to +4.5, with average fertility designated as 0.0.

Bulls providing seminal plasma were subjected to a regular semen collection schedule, dictated by the AI center, which typically amounted from one to three ejaculates per week. A single ejaculate was analyzed from each bull without regard to month, season or order in a sequence of ejaculates. The date the seminal plasma was taken was within the window of time used to calculate the fertility of the bull.

Within 15 min of collecting the ejaculate, semen was centrifuged (1,000×g, 15 min) and the supernatant seminal plasma transferred to cryovials (#72,694,007 Sardstedt, Princeton, N.J.) for storage in liquid nitrogen. Samples were shipped in liquid nitrogen from the AI center to our laboratory where they remained in liquid nitrogen storage until analyzed. After thawing at ambient temperature, seminal plasma samples were recentrifuged (10,000×g, 60 min at 5° C.), assayed for protein concentration [Lowry OH, Rosebrough WJ, Farr AL, Randall RJ., 1951, Protein measurement with Folin phenol reagent. J. Biol. Chem., Vol. 193, pp 265–275], divided into aliquots and refrozen in liquid nitrogen. Immediately prior to performing electrophoresis, samples were thawed at ambient temperature.

EXAMPLE 2

Identification of Proteins Correlated with Fertility

One-dimensional polyacrylamide gel electrophoresis of seminal plasma was performed under denaturing conditions using standard methods previously described [Hames BD., 1981, An introduction to polyacrylamide gel electrophoresis. In: Hames B, Rickwood D (eds.), Gel Electrophoresis, A Practical Approach. Washington, D.C.: IRL Press; pp 1–86]. Seminal plasma samples were subjected to two-dimensional polyacrylamide gel electrophoresis according to the method of O'Farrell [O'Farrell PH. High resolution two-dimensional electrophoresis of proteins. J Biol Chem 1975; 250:4007–4021] as modified for use in our laboratory. The isoelectric focusing tube gels contained a mixture of ampholytes consisting of 0.4 ml of pH 3–7 and 0.1 ml of pH 3–10 (Serva, Heidelberg, Germany) to establish a pH gradient. Tube gels were prefocused at a constant voltage of 200 V for 15 min, 300 V for 30 min and 400 V for 30 min. Samples of seminal plasma consisting of 400–500 μg protein in less than 50 μl were solubilized in urea and beta-mercaptoethanol giving a final volume of 100 μl to be loaded onto the gel. Tube gels then were electrofocused for 20 h at 375 V, followed by 1 h at 800 V. After extruding electrofocused gels from the tubes, they were placed on 4% stacking gels covering the top of 10–17.5% acrylamide gradient slab gels using 1% molten agarose to seal them in position. Molecular weight standards (Sigma Chemical Co., St. Louis, Mo.) were electrophoresed in the second dimension along with the proteins originating from the isoelectric focusing gel. The standards were myosin (205 kDa), β-galactosidase (116 kDa), phosphorylase B (97 kDa), bovine serum albumin (66 kDa), ovalbumin (45 kDa) and carbonic anhydrase (29 kDa).

Gels were stained overnight in 0.125% Coomassie Brilliant Blue R-250 (Sigma), 50% methanol and 10% acetic acid in distilled water. Gels were destained in 25% methanol and 10% acetic acid, and photographed with LPD-4 positive film (Kodak, Rochester, N.Y.). One positive film of each gel for each bull was scanned with a Bio-Rad model 620 densitometer (BioRad, Rockville Centre, N.Y.), interfaced with a Dell system 310 computer. These data were used to prepare a map of the proteins present in each gel and objectively estimate the amount of each protein.

The fertility-associated protein densities were adjusted by subtracting the average background for each gel image from the protein densities of interest. Densities for each fertility-associated protein then were compiled and average (±SE) protein density was calculated for bulls grouped by fertility level.

Densities of the four fertility-associated proteins of each bull also were used as a database to develop a model to predict bull fertility. Several regression models were evaluated for providing the best empirical prediction of fertility. Evaluations were made on log and square root transformations of protein densities. The criteria for comparing models were R-squared, adjusted R-squared, C-P and multicollinearity [Neter J, Wasserman W, Kutner MH. Applied Linear Statistical Models; RD Irwin Inc, Homewood, Ill.; 1985].

Figure 2A:
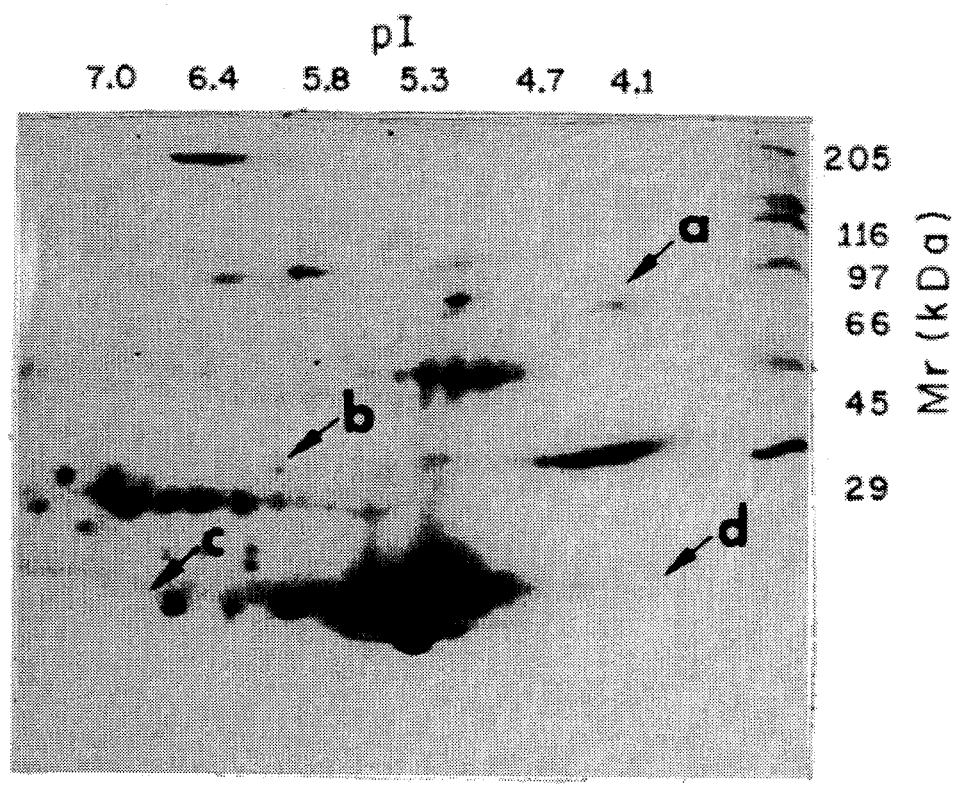
FIG. 2(a) Representative two-dimensional polyacrylamide gels of seminal plasma proteins from a higher fertility bull. Locations of fertility associated proteins are indicated with arrows. a, 55 kDa, 4.1 pI; b, 26 kDa, 6.2 pI; c, 16 kDa, 6.7 pI and d, 16 kDa, 4.1 pI.
Figure 2B:
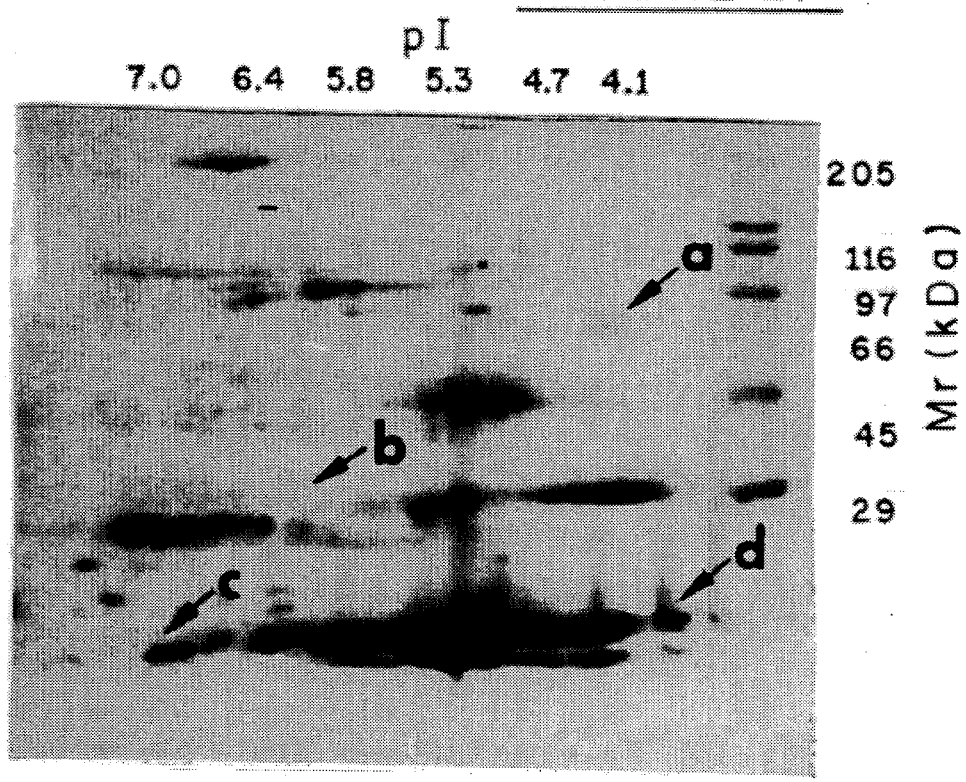
FIG. 2(b). Representative two-dimensional polyacrylamide gels of seminal plasma proteins from a lower fertility bull. Locations of fertility associated proteins are indicated with arrows. a, 55 kDa, 4.1 pI; b, 26 kDa, 6.2 pI; c, 16 kDa, 6.7 pI and d, 16 kDa, 4.1 pI.
Figure 3:
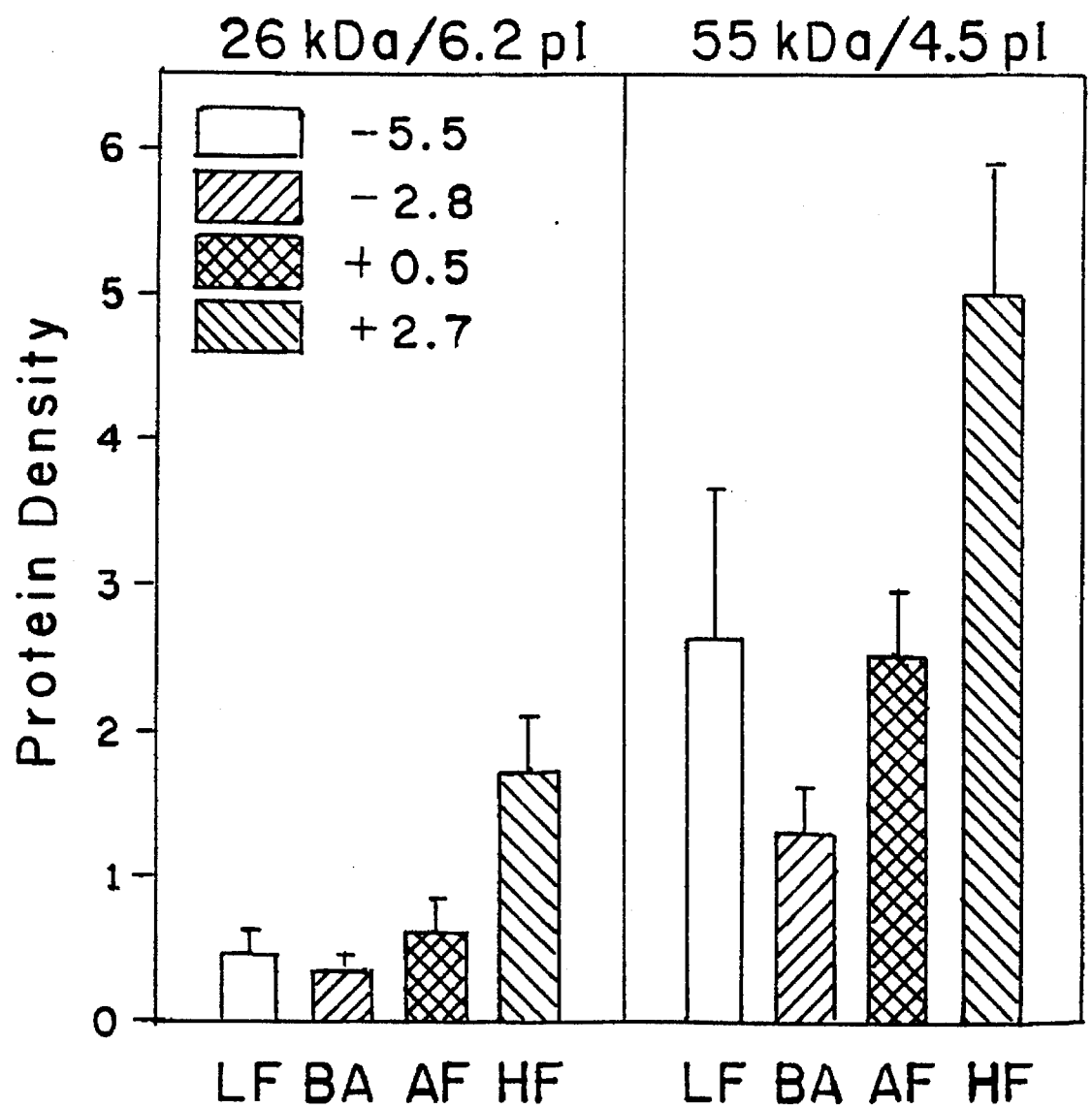
FIG. 3. Average densities (±SE) of the high fertility proteins determined in 2-D gels of seminal plasma for bulls grouped by fertility. Low fertility (LF), (−5.5, n=6); below average (BA), (−2.8, n=7), average fertility (AF), (+0.5, n=11) and high fertility (HF), (+2.7, n=11).

Preliminary studies with two different ejaculates from each of three bulls indicated similar protein profiles on one- and two-dimensional electrophoresis gels between ejaculates from the same bull and indicated virtually identical profiles between replicate gels of the same ejaculate. Therefore, only one ejaculate was evaluated from each bull in subsequent studies. Densitometry data of one-dimensional SDS-PAGE of seminal plasma from bulls of differing fertility did not provide consistent evidence for differences in protein banding patterns associated with fertility. Although visual inspection of two-dimensional gels of seminal plasma from the 35 bulls indicated some variation in protein maps among individuals, four different polypeptides appeared to occur in association with bull fertility level. Two proteins (26 kDa, pI 6.2; 55 kDa, pI 4.5) occurred with greater frequency and density in bulls of higher fertility (FIG. 2(a)) and two proteins (16 kDa, pI 4.1; 16 kDa, pI 6.7) were more prominent in lower fertility bulls (FIG. 2(b)). Based on these preliminary observations, we subjected all two-dimensional gels to analysis by video densitometry to obtain quantitative data on the polypeptides of interest. The density and area of the individual polypeptides on the gel were determined for each bull sample, and these quantitative data were summarized for bulls combined by fertility level into four groups. Seminal plasma from bulls in the high fertility group (HF), ranging from 2.0 to 4.5 percentage points above average fertility, had significantly more ($p<0.05$) of the 26 kDa protein compared with seminal plasma from bulls in the average fertility (AF; +1.4 to −0.2 percentage points), below average fertility (BA; −2.3 to −3.8), and low fertility (LF; −4.3 to −6.6) groups (FIG. 3). HF bull seminal plasma also had more of the 55 kDa protein than seminal plasma of AF and BA bulls.

Figure 4:
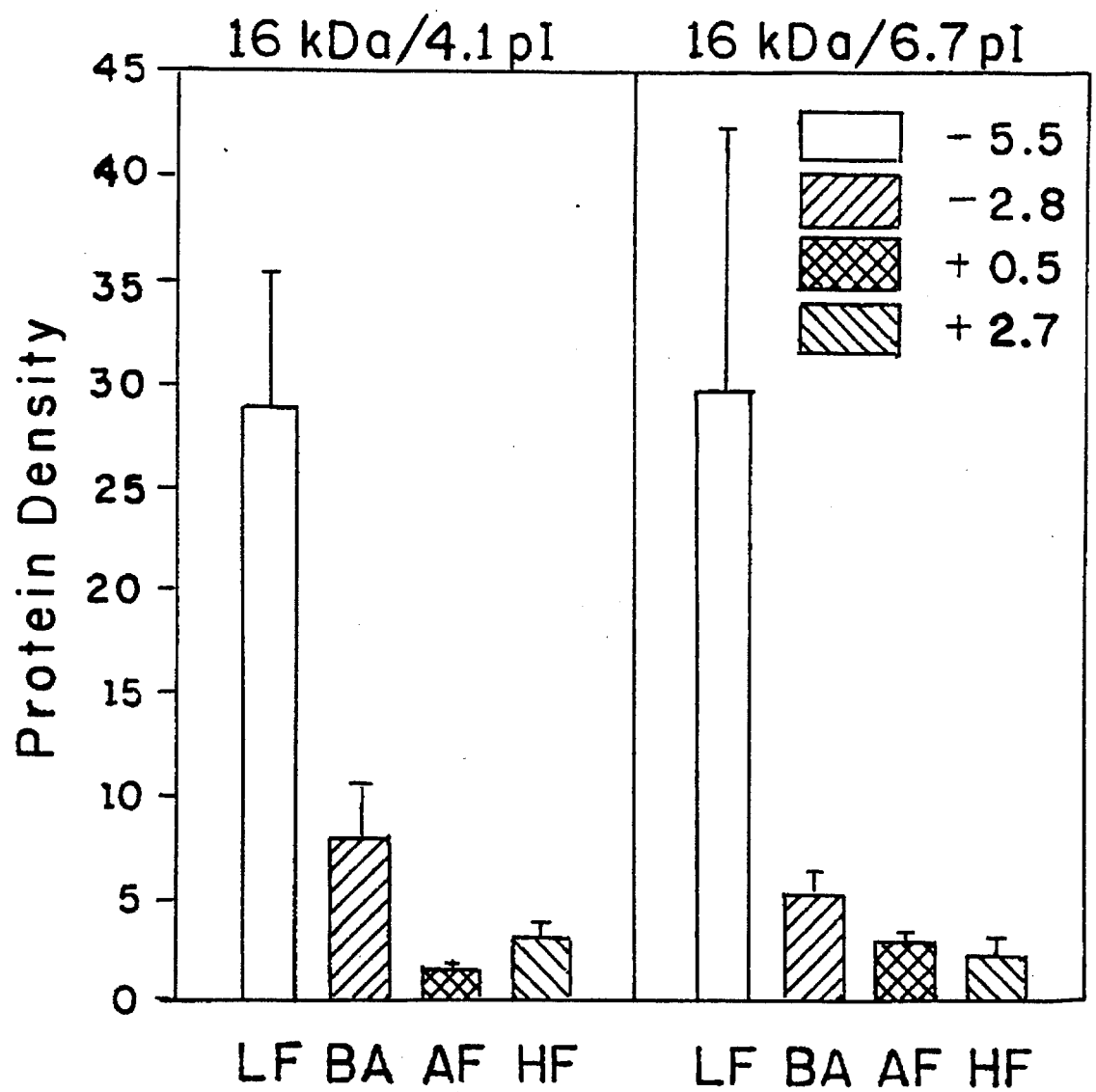
FIG. 4. Average densities (±SE) of the low fertility proteins determined in 2-D gels of seminal plasma for bulls grouped by fertility. Low fertility (LF), (−5.5, n=6); below average (BA), (−2.8, n=7), average fertility (AF), (+0.5, n=11) and high fertility (HF), (+2.7, n=11).

BA and LF bulls had significantly more ($p<0.05$) of the 16 kDa, pI 4.1 protein than AF and HF bull seminal plasma (FIG. 4), HF bulls had significantly more ($p<0.05$) of the protein than AF bull seminal plasma. LF bulls had significantly more of the 16 kDa, pI 6.7 protein than AF, BA and HF bulls, and BA bull seminal plasma had significantly more ($p<0.05$) of the 16 kDa, pI 6.7 protein than AF and HF bulls.

EXAMPLE 3

Fertility Prediction

The regression model which provided the best empirical prediction of fertility based on the four fertility-associated proteins in seminal plasma was:

$$\text{Fertility} = -2.12 + 3.58\sqrt{D_1} - 0.90\sqrt{D_2} + 1.61\sqrt{D_3} + 0.35\sqrt{D_4} - 1.69\sqrt{eeD_1} \cdot \sqrt{+e, radD_4}$$

Fertility represents the predicted percentage point deviation from the average fertility of bulls at an AI center, and $D_1$ through $D_4$ represent the densities of the fertility-associated proteins: 26 kDa, pI 6.2; 16 kDa, pI 4.1; 55 kDa, pI 4.5; 16 kDa, pI 6.7, respectively. The model used square root transformations of the protein densities. Although the main effect of the square root of $D_4$ was not significant, it was retained in the model because of a significant interaction between the square roots of $D_1$ and $D_4$.

Figure 5:
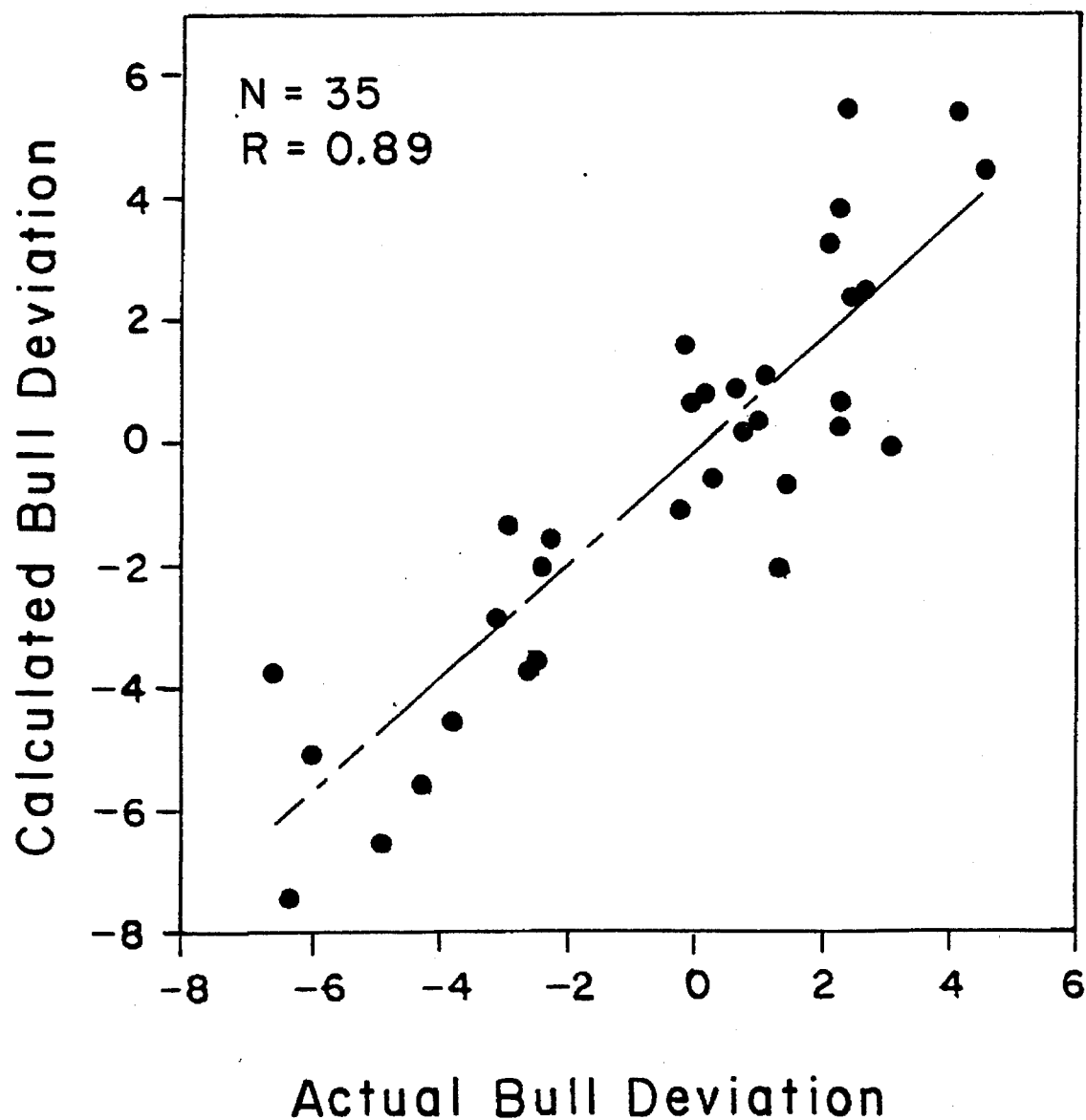
FIG. 5. Plot of the actual bull fertility (percentage point deviation from the mean) versus the calculated fertility values for the 35 bulls undergoing analysis of seminal plasma by two-dimensional gel electrophoresis.

Estimated fertility values for each bull were generated by comparison to a data set which included seminal plasma fertility protein data from the 34 other bulls in the study. A plot of actual in vivo fertility versus calculated fertility (FIG. 5) was linear, and there was a positive correlation ($r=0.89$) indicating that the predictive model was valid over the range of bull fertilities studied.

Calculated and actual fertility values differed by an average of 1.19±0.15 percentage points over all bulls. Average percentage point differences (mean±SE) between the calculated and actual fertility values among fertility groups were

EXAMPLE 4

Zona-Free Bovine Oocytes Fertility Assay

The zona-free bovine oocyte fertility assay was performed in the following fashion. Oocytes were matured in vitro using the methods of Sirad et al. [Sirad, M. A., J. J. Parrish, C. B. Ware, M. L. Leibfried-Rufiedge and N. L. First. 1988. The culture of bovine oocytes to obtain developmentally competent embryos. Biol. Reprod. 39:546–552] and McNutt, T. L. and G. J. Killian [1991. Influence of bovine follicular and oviductal fluids on sperm capacitation in vitro. J. Androl. 12:244–252]. Ten cumulus oocyte complexes (COC) were matured in each 50 µl drop of maturation medium in 60 mm petri dishes under heavy paraffin oil. After incubation for 21 h at 39° C. in an atmosphere of 5% $CO_2$ in air, COC were removed from the maturation microdrops and vortexed for 3 min in 0.5 ml microfuge tubes to remove the cumulus cells. Zonae were removed from cumulus-free, matured oocytes by incubation in 0.1% pronase (Type XIV-bacterial; Sigma #P-5147, St. Louis, Mo.) in PBS for 2–5 min with careful observation. Oocytes were then washed 3 times in a low bicarbonate HEPES medium and transferred in groups of 10 to 50 µl drops of fertilization medium [Bavister, B. D. 1981. Substitution of a synthetic polymer for protein in a mammalian gamete culture system. J. Exp. Zool. 217:45–51] under heavy mineral oil. Dishes were inseminated with $0.125 \times 10^6$ sperm and incubated for 12–15 h. After coincubation with sperm stained with fluorescent dyes, eggs were washed in a low bicarbonate HEPES medium. After fixation for 1 min in neutral buffered formalin and treatment with SLOWFADE antiquenching solution (Molecular Probes Inc., Eugene, Oreg.) oocytes were mounted on slides and stored in a humidified chamber protected from fight at 4° C. The slides were examined with an Olympus BH-2 microscope equipped with a BH2-RFC for reflected fight fluorescence.

EXAMPLE 5

Sperm Preparation and Capacitation

Bulls providing semen for the study were housed in barris during the course of the experiment. Cull bulls were obtained from three artificial insemination (AI) centers in the northeastern United States. Fertility data for each bull were available from breeding records provided by the AI centers. Data were normalized to account for minor differences among the AI centers in calculating fertility, and are reported as a percentage point deviation from the average bull fertility of that center.

Semen was collected from bulls using an artificial vagina. When sperm were to be mixed with seminal plasma from different bulls, sperm in 1 ml of semen were washed once by centrifugation (500 g for 10 min) in a 1:10 ratio with a protein-free, modified Tyrode's medium (MTM; Parrish, J. J., J. L. Susko-Parrish, M. A. Winer and N. L. First., 1988, Capacitation of bovine sperm by heparin. Biol. Reprod. Vol. 38, pp 1171–1180) containing 1 mg/ml polyvinyl alcohol. The remainder of the ejaculate was centrifuged at 2300 g for 10 min. The supernatant was removed and recentrifuged at 2300 g for 10 min to remove remaining sperm from the seminal plasma. The washed sperm were recombined with homologous seminal plasma or heterologous seminal plasma in a ratio approximating that of the original ejaculate and incubated for 30 min at 37° C. The pool of low fertility seminal plasma used in the second series of experiments was prepared by combining equal amounts of the seminal plasma from an ejaculate of each of three different subfertile bulls. These bulls ranged in fertility from 18.1 to 11.7 percentage points below the AI center average and were different from the low fertility bulls providing ejaculated sperm for the experiments. For capacitation, sperm were washed in MTM (500g for 10 min) and then incubated ($50 \times 10^6$ cells/ml) for 4 h (39° C.; 5% $CO_2$ in air) in MTM+10 µg/ml heparin. Capacitated sperm then were induced to acrosome react by 10 min incubation at 39° C. with 60 µg/ml lysophosphatidylcholine (LPC;Sigma #L-5004;), and then used to inseminate microdrops containing zona-free bovine oocytes.

EXAMPLE 6

Sperm Staining

Stock solutions of fluorescent isothiocyanate-isomer I (FITC; F-1906;Molecular Probes, Inc.) and tetramethyl-rhodamine isothiocyanate (TRITC; R-491; Molecular Probes Inc.) were prepared following the method of Parrish and Foote (Parrish, J. J. and R. H. Foote., 1985, Fertility differences among male rabbits determined by heterospermic insemination of fluorochrome-labeled spermatozoa. Biol. Reprod., Vol. 33, pp 940–949). Stock stain solutions were diluted (0.1 mg/ml) with phosphate-buffered saline supplemented with glucose (PBSG). All sperm were stained with Hoechst 33342 (H-1399; Molecular Probes Inc.; 0.5 µg/ml), 1 h before the end of the 4 h capacitation period to visualize sperm head decondensation and pronuclear development. To distinguish the sperm treatment, FITC (0.5 µg/ml) or TRITC (0.75 µg/ml) was added to the incubation tubes 10 min before the end of capacitation. Sperm were then washed twice in fresh MTM and combined in the desired treatment combination at the time of LPC incubation. This procedure permitted identification of the treatment of each sperm which penetrated an egg and did not affect sperm motility or ability to penetrate zona-free bovine oocytes when compared to unstained controls (Henault, M. A. and G. J. Killian., 1992, Relationship between bull fertility and in vitro penetration of zona-free bovine oocytes. Animal Science Abstract].

Statistical Analyses

To determine if a significant advantage of a particular sperm type existed when two types of sperm were competed to penetrate the same eggs, the McNemar's test, a form of categorical data analysis [Fleiss J. L., 1973: Statistical Methods for Rates and Proportions. John Wiley and Sons. N.Y., London, Sydney, Toronto. pp 72–91] was used. P-values were obtained by evaluation of Z scores obtained from analyzing the data. A p-value of $\leq 0.05$ was considered statistically significant. This statistical procedure allowed the evaluation of penetrations of both types of sperm within each oocyte.

The present invention describes the existence of four fertility-associated proteins in bovine seminal plasma that appear to be of value in predicting small differences in relative fertility among bulls. The bulls studied represented a population of reproductively normal males with normal semen parameters. Because similar numbers of sperm from each bull were used to inseminate the females, the effect of sperm numbers on fertility was similar among bulls. Although studies with other species have reported the presence of factors in seminal plasma related to in vivo fertility, the males being compared were typically categorized as fertile or infertile, with the infertile males often oligo- or azospermic. Because the absence or reduction in sperm numbers in the infertile male could contribute to infertility, the biological significance of differences in seminal plasma composition associated with fertility was unclear.

Although the results described herein demonstrate a high correlation between the amount of certain seminal plasma proteins and bull fertility, it is not known whether this relationship is cause and effect, or coincidental. Furthermore, it is important to note that the differences in amount of fertility-associated proteins observed in a gel based on staining intensity may reflect post-translational modifications of proteins rather than more or less of a protein, or different proteins per se.

It is known that seminal plasma proteins become associated with sperm membranes at the time of ejaculation. Attempts to remove these proteins from rabbit sperm indicate that binding of some seminal plasma proteins to the sperm membranes is quite strong. This may explain our inability to dramatically improve the fertility of ejaculated sperm from subfertile bulls by washing and mixing them with seminal plasma from high fertility bulls. The results of the ten comparisons showed an equal occurrence of oocyte penetrating advantages by sperm incubated in high or low fertility seminal plasma. The 6 instances where a particular type of sperm had a statistically significant oocyte penetrating advantage also were evenly divided between sperm exposed to high and low fertility seminal plasma. Prior exposure of sperm to seminal plasma proteins at ejaculation may compromise later attempts to replace membrane bound seminal proteins by mixing with seminal plasma from another bull.

The observation that high fertility sperm mixed with low fertility seminal plasma had significantly fewer penetrations than high fertility sperm incubated in homologous seminal plasma or low fertility sperm mixed with homologous low fertility seminal plasma are important. These results may indicate that low fertility seminal plasma contains antifertility factors which have a greater negative effect on high fertility sperm than low fertility sperm. Prior exposure of low fertility sperm to negative factors in their own seminal plasma may preclude further reduction in fertility after exposure to foreign low fertility seminal plasma. This conclusion is supported by the experiments done using pooled low fertility seminal plasma foreign to the subfertile bulls being tested. Although the differences between high and low fertility bulls were no longer significant, high fertility sperm probably had decreased fertility. This conclusion was reached since the penetration assay used has been shown to detect small differences in fertility of ejaculated sperm from high and low fertility bulls.

Although antifertility factors in seminal plasma have been reported for many species actual reports of differences between seminal plasma of high and low fertility individuals are limited. Alterations in seminal plasma protein distribution between fertile and subfertile individuals also have been noted in humans and differences in heparin binding proteins correlated with fertility in the bull. It is possible that them are fertility or antifertility factors in seminal plasma that bind to sperm at the time of ejaculation. These seminal plasma constituents may not be removed from the sperm by routine washing, since our results show that prior exposure to a particular type of seminal plasma may predetermine the fertility of sperm. Also, this fertility cannot be significantly changed by simple washing and exposure to seminal plasma of contrasting fertility, with the possible exception of the fertility lowering effects of low fertility seminal plasma.

The exact components of seminal plasma which were responsible for the effects we observed are yet to be identified. This study, however, presents definitive proof that exposure to seminal plasma is of significant importance in determining the fertility of ejaculated sperm.

Thus, while we have illustrated and described the preferred embodiment of our invention, it is to be understood that this invention is capable of variation and modification, and we, therefore, do not wish or intend to be limited to the precise terms set forth, but desire and intend to avail ourselves of such changes and alterations which may be made for adopting the invention of the present invention to various usuages and conditions. Accordingly, such changes and alterations are properly intended to be within the full range of equivalents and, therefore, within the purview of the following claims. The terms and expressions which have been employed in the foregoing specification are used therein as terms of description and not of limitation, and thus there is no intention in the use of such terms and expressions of excluding equivalents of features shown and described or portions thereof, it being recognized that the scope of the invention is defined and limited only by the claims which follow.

Thus is described our invention and the manner and processing of making and using it in such full, clear, concise, and exact terms so as to enable any person skilled in the art to which it pertains, or with which it is most nearly connected, to make and use the same.

What is claimed is:

1. A method of predicting bovine male fertility comprising the steps of:
   (I) measuring the relative concentration of each of the following four proteins found in seminal plasma of a semen sample taken from a donor;
      (a) molecular weight 55 kDa and isoelectric point 4.5 pI
      (b) molecular weight 26 kDa and isoelectric point 6.2 pI
      (c) molecular weight 16 kDa and isoelectric point 6.7 pI
      (d) molecular weight 16 kDa and isoelectric point 4.1 pI
   (II) correlating the concentrations of the four proteins to the fertility of the donor of the semen sample according to the following formula:

$$F=-2.12+3.58\sqrt{D_1}-0.90\sqrt{D_2}+1.61\sqrt{D_3}+0.35\sqrt{D_4}-1.69\sqrt{+eeD_1}\cdot\sqrt{+e,radD_4}$$

wherein "F" is predicted fertility expressed as a deviation from the average fertility of bulls, and $D_1$, $D_2$, $D_3$ and $D_4$ represent the relative concentration of the proteins described in (a), (b), (c), and (d) respectively, wherein the relative concentration is represented as a fraction of said proteins to the concentration of the four measured proteins in the seminal plasma; and
   (III) determining the fertility of the donor by comparing "F" to the average fertility values of a known bovine male population.

2. A method according to claim 1, wherein the measuring of the relative concentration of the proteins is done individually by two-dimensional polyacrylamide gel electrophoresis of said semen sample.

* * * * *